United States Patent [19]

Gold

[11] Patent Number: 4,867,978

[45] Date of Patent: Sep. 19, 1989

[54] METHOD OF PROLONGING CANCEROUS PATIENT SURVIVAL IN HUMANS WITH HYDRAZINE SULFATE

[76] Inventor: Joseph Gold, 127 Edgemont Dr., Syracuse, N.Y. 13214

[21] Appl. No.: 276,059

[22] Filed: Nov. 25, 1988

Related U.S. Application Data

[63] Continuation-in-part of Ser. No. 201,083, Jun. 1, 1988, abandoned, which is a continuation of Ser. No. 32,051, Mar. 27, 1987, abandoned.

[51] Int. Cl.⁴ ............................................. A61K 33/02

[52] U.S. Cl. ..................................... 424/719; 424/709

[58] Field of Search ......................................... 424/166

[56] References Cited

U.S. PATENT DOCUMENTS 4,110,437 8/1978 Gold .................................. 424/166

Primary Examiner—Jerome D. Goldberg

[57] ABSTRACT

Hydrazine sulfate, alone or formulated with liquid or solid carriers, will prolong patient survival when administered to early-stage human cancer patients parenterally or orally.

7 Claims, No Drawings

METHOD OF PROLONGING CANCEROUS PATIENT SURVIVAL IN HUMANS WITH HYDRAZINE SULFATE

This application is a continuation-in-part of pending Ser. No. 201,083, filed June 1, 1988, now abandoned, which is a continuation of Ser. No. 032,051, filed Mar. 27, 1987, now abandoned.

BACKGROUND OF THE INVENTION

Many different types of chemical compounds have been used in the past to retard or inhibit various tumors in man. More than thirty compounds are approved for use in cancer therapy in various countries, but the achievement of therapeutic benefit has reached a plateau, and the search for antitumor agents continues in various directions.

In 1967, Weitzel and co-workers reported in the Zeitschrift fuer Physiologische Chemie, 348, 433–442 that hydrazine acetate and sulfate inhibit in vivo the growth of ascites carcinoma and sarcoma 180 in the mouse and Walker carcinosarcoma in the rat. It is well known that the results from lower animals cannot be extrapolated in humans. Indeed, the experience at the U.S. National Institutes of Health has been that more than 200 new chemotypes having anticancer activity in animals have failed to show clinically useful anticancer activity in humans, as shown in the following table (Table I was compiled from various reports of the U.S. National Cancer Institute):

TABLE I

| New Chemotypes evaluated against cancer 1960–1985 ||
|---|---|
| Succeeded | Failed |
| Adriamycin | |
| Cisplatin | Tripdiolide |
| Bleomycin | Maytansine |
| Mitomycin | Sangivamycin |
| Vincristine | Pentamethylmelamine |
| Cyclophosphamide* | Taxol |
| Etopside** | Bactobolin |
| | Alanosine |
| | PALA |
| | Acivicin |
| | Methyl GAG |
| | Menogarol |
| | Triciribine |
| | Disuccinimide |
| | Flavoneacetic acid |
| | Teroxirone |
| | Acodazole |
| | Benzisoquinolinedione |
| | Didemnin B |
| | Phyllanthoside |
| | Ellipticine |
| | Emetine |
| | Indicine-N—oxide |
| | Bouvardin |
| | Thalicarpine |
| | Tetrandrine |
| | Acronycine |
| | Tylocrebrine |
| | Lapachol |
| | Nitidine |
| | Neocarzinostatin |
| | Macromomycin |
| | Largomycin |
| | Streptimidone |
| | Valinomycin |
| | Piperazinedione |
| | Fagaronine |
| | Coralyne |
| | Benzophenanthridine |
| | Camptothecin |
| | Acosamine |

TABLE I-continued

| New Chemotypes evaluated against cancer 1960–1985 ||
|---|---|
| Succeeded | Failed |
| | Acylagmatine |
| | Allamandicin |
| | Allamandin |
| | Agolosamine |
| | Anguidine |
| | Angustmycin |
| | Ansamycin |
| | Aureolic acid |
| | Baccharin |
| | Bakkenolide |
| | Baumycin |
| | Bisnorditerpene |
| | Bouvardin |
| | Bredenine |
| | Bruceolide |
| | Bryogenin |
| | Bufadienolide |
| | Cardenolides |
| | Catharanthus |
| | Cephalotaxine |
| | Chapparinone |
| | Coformycin |
| | Colcemid |
| | Colchicine |
| | Colubrinol |
| | Coralyne |
| | Cucurbitacin |
| | Daphnetoxin |
| | Datiscacin |
| | Cecoyinine |
| | Angustmycin |
| | Scirpenol |
| | Isobruceine |
| | Nitidine |
| | Duborimycin |
| | Elemanolide |
| | Elephantopin |
| | Ellipticine |
| | Elephantopin |
| | Enteromycin |
| | Eremantholides |
| | Eriofertopin |
| | Eudesmanolides |
| | Eupacunin |
| | Euparotin |
| | Fabacein |
| | Fagaronine |
| | Fusarenon |
| | Germacranolide |
| | Glaucarubinone |
| | Guaianolide |
| | Helenolin |
| | Homoerythrina |
| | Hycanthone |
| | Picrasin |
| | Iridoid lactone |
| | Isobruceine |
| | Isocucurbitacin |
| | Isoplumericin |
| | Iatrophone |
| | Lapachol |
| | leurosidine |
| | Leurosine |
| | Liatrin |
| | Masine |
| | Maysenine |
| | Maytanbutacine |
| | Maytanbutine |
| | Maytanprine |
| | Maytanvaline |
| | Miracil D |
| | Mitrymicin |
| | Mycophenolic acid |
| | Neosolaneol |
| | Nitidine |
| | Nivalenol |
| | Normaysine |
| | Oxazinomycin |
| | Peltatin |

TABLE I-continued

New Chemotypes evaluated against cancer 1960–1985

| Succeeded | Failed |
|---|---|
| | Penstemide |
| | Phleomycin |
| | Picrasane |
| | Picropodophyllin |
| | Piptocarphins |
| | Plumericin |
| | Porfiromycin |
| | Pseudoguaianolides |
| | Puromycin |
| | Pyrazomycin |
| | Quadrone |
| | Quassimarin |
| | Roridin |
| | Samaderine |
| | Sangivamycin |
| | Eudesmanolide |
| | Showdomysin |
| | Sikkimototoxin |
| | Simalikalactone |
| | Simaroubolide |
| | Stachybotrytoxin |
| | Steganacin |
| | Streptonigrin |
| | Taxodione |
| | Tenulin |
| | Tetrandrine |
| | Thalicarpine |
| | Trichodermin |
| | Undulatone |
| | Vernolepin |
| | Verrucarin |
| | Vincadioline |
| | Vindoline |
| | Withaferin |
| | Withanolide |
| | Phosphonoacetic acid |
| | Pentostatin |
| | Deazaguanine |
| | Tiazofurin |
| | Ocodazole |
| | Bisbenzimidazole |
| | ICRF |
| | JB-11 |
| | Dihydrotriazine benzene sulfonyl fluorid |
| | Glyoxylic acid sulfonylhydrazone |
| | N—Methylformamide |
| | Caracemide |
| | Isopropylpyrrolizine deriv. |
| | Phyllanthoside |
| | Aphidicolin |
| | Largomycin |

*Analog of nitrogen mustard
**Analog of podophyllotoxin

In addition, hundreds of analogs of the new and old chemotypes have failed to show anticancer activity in man, in spite of good antitumor activity in animals. In contrast to the above, only about five new chemotype anticancer drugs have reached the market in the last 25 years. Hence, early reports that hydrazine sulfate had antitumor activity in animals did not serve to predict that it might have anticancer activity in humans.

Because of this poor predictability of animal models, the National Cancer Institute of the U.S. National Institutes of Health has now abandoned the mouse model after 25 years of unproductive trial and is instituting a new in vitro program for discovering new antitumor drugs (E. Eckholm, New York Times, Dec. 23, 1986, p. C1).

A total inventory of cancer drugs approved for sale in the United States is set forth in Table II, and it will be seen that most of these are analogs of other drugs. Table III shows that, with one exception, all of the recent New Drug Applications filed for anticancer drugs led to unapprovable ratings by the U.S. Food and Drug Administration. Table IV shows that the last new chemotype which succeeded in the clinic was discovered more than 20 years ago.

TABLE II

Anticancer Drugs Approved in U.S. in Order of Approval by FDA

| | | |
|---|---|---|
| leuprolide - Lupron (gonadotropin releasing hormone) | Takeda-Abbott | 4/9/85 |
| etoposide - Vepesid | BMY | 11/10/83 |
| streptozotocin - Zanosar | Upjohn | 7/7/82 |
| estramustine - Emcyt | Roche | 12/24/81 |
| daunorubicin - Cerubidine | Ives | 12/19/79 |
| cisplatin - Platinol | BMY | 12/19/78 |
| tamoxifen - Nolvadex (antiestrogen) | ICI | 12/30/77 |
| carmustine | BiCNU | 3/7/77 |
| lomustine - CEENU | BMY | 8/4/76 |
| dacarbazine - DTIC-Dome | Miles | 5/27/75 |
| doxorubicin - Adriamycin | Farmitalia | 8/7/74 |
| mitomycin C - Mutamycin | BMY | 5/28/74 |
| bleomycin - Blenoxane | BMY | 7/31/73 |
| megestrol acetate - Megace | BMY | 8/18/71 |
| floxuridine - FUDR | Roche | 12/18/70 |
| mitotane - Lysodren | BMY | 7/8/70 |
| plicamycin - Mithracin | Pfizer | 5/5/70 |
| procarbazine - Matulane | Roche | 7/22/69 |
| cytarabine - Cytosar U | Upjohn | 6/17/69 |
| testolactone - Teslac | Squibb | 6/3/69 |
| hydroxyurea - Hydrea | Squibb | 12/7/67 |
| pipobroman - Vercyte | Abbott | 7/1/66 |
| melphalan - Alkeran | BW | 1/17/64 |
| vincristine - Oncovin | Lilly | 7/10/63 |
| uracil mustard - Uracil Mustard | Upjohn | 9/13/62 |
| 5-fluorouracil - Fluorouracil | Roche | 4/25/62 |
| dromostanolone - Drolban | Lilly | 10/26/61 |
| vinblastine - Velban | Lilly | 3/6/61 |
| cyclophosphamide - Cytoxan | BMY | 11/16/59 |
| thiotepa - Thio-Tepa | Lederle | 3/9/59 |
| chlorambucil - Leukeran | BW | 3/18/57 |
| busulfan - Myleran | BW | 6/26/54 |
| methotrexate - Methotrexate | Lederle | 12/7/53 |

A review of the FDA's New Drug Evaluation - Statistical Report (March 1986) shows that no novel anticancer drug is pending approval at the FDA.

TABLE III

The following are the dispositions of antineoplastics filed in 1980 to 1984:

| | | | |
|---|---|---|---|
| Filed in 1980 | Not approvable | NDA No. 18-348 | Antineoplastic |
| | Not approvable | NDA No. 18-529 | Antineoplastic |
| | Not approvable | NDA No. 18-554 | Antineoplastic |
| Filed in 1981 | Not approvable | NDA No. 18-641 | Antineoplastic |
| | Not approvable | NDA No. 18-653 | Antineoplastic |
| Filed in 1982 | Not approvable | NDA No. 50-569 | Antineoplastic |
| Filed in 1984 | Not approvable | NDA No. 50-595 | Antineoplastic |

Table IV lists the anticancer drugs approved in the United States. The last non-hormonal anticancer agent to be approved in the U.S. was etoposide in 1983.

The following are the years of discovery of the major anticancer drugs on the U.S. market (arbitrarily assumed to be one year before the first publication):

TABLE IV

| | |
|---|---|
| Etoposide | 1966 |
| Adriamycin | 1966 |
| Bleomycin | 1966 |
| Cisplatin | 1965 |
| Mitomycin C | 1965 |
| Vincristine | 1961 |
| 5-Fluorouracil | 1957 |
| Cyclophosphamide | 1957 |
| Methotrexate | 1949 |

Thus, there have been no new chemotype cytotoxic anticancer drugs discovered in the past twenty years. Consequently, there remains an unfulfilled need for additional cancer drugs for clinical use against tumors in humans.

Up the present time, it has been generally unrecognized that a specific anticachexia agent (by virtue of its ability to interrupt those specific thermodynamic metabolic processes leading to cancer cachexia) possesses antitumor potential, by virtue of a systematic thermodynamic interrelationship between tumor progression (tumor energy gain) and cancer cachexia (host energy loss); this has been taught in the scientific literature since 1974 (J. Gold, Cancer Cachexia and Gluconeogenesis, Ann. N.Y. Acad. Sci., 230, 103–110 (1974)). Thus, while it is true that any antitumor agent may have anticachexia potential, if curative, it is also true that a specific anticachexia agent may have potential for increased patient survival. However, it is not obvious, nor predictable, from the prior art that hydrazine sulfate would possess this potential.

In 1978, the present inventor was issued U.S. Pat. No. 4,110,437 for the treatment of cancer cachexia with hydrazine sulfate. Investigations were also undertaken to ascertain whether hydrazine sulfate could retard tumor growth in humans. However, these early studies were inadequate and failed to statistically demonstrate antitumor activity.

A group at Sloan-Kettering concluded after a trial that: "The clinical observations recorded in this report fail to support a role for hydrazine sulfate as an anticancer agent. We conclude that its clinical utilization is not warranted at present and do not plan further trials."(Ochoa et al., Cancer Chemotherapy Reports, Part 1, Vo. 59, No. 6, Nov./Dec. 1975; pp. 1151–1154).

In addition, a group at the University of Virginia repoted that: "Hydrazine sulfate as administered in this series failed to demonstrate any objective or subjective antitumor activity and no further trials are currently planned."(Lerner and Regelson, Cancer Treatment Reports, Vol. 60, No. 7, July 1976, pp. 959–966). Another later publication by Regelson et al. stated: "In conclusion, we feel that hydrazine sulfate as given in this study is an inactive compound."(Cancer Chemother. Pharmacol., 3, 121–124, 1979).

Thus, the prior art taught that hydrazine sulfate appeared to be inactive against primary tumor growth in man.

SUMMARY OF THE INVENTION

This invention is based on the discovery that hydrazine sulfate, when administered parenterally or orally in effective, non-toxic amounts to humans with tumors of the lung, prostate, breast, ovaries, thyroid, pancreas, lymph, cervix, gastrointestinal tract and other sites will significantly prolong survival of early-stage human cancer patients, while improving the patient's quality of life.

DETAILED DESCRIPTION OF THE INVENTION

The dosages of hydrazine sulfate employed in the present invention can vary from 1 to 5 mg/kg daily, which is well below the LD50 and has been found to be well tolerated in the majority of early-stage patients so treated for periods of up to four years.

Preferably, the regimen followed is one 60 mg capsule of hydrazine sulfate daily for the first three days, then two such capsules daily for the next three days, and then three 60 mg capsules each day thereafter. In actual practice, patients weighing over 130 pounds do well on three or four 60 mg capsules daily. For patients weighing less than 100 pounds, the regimen followed is preferably one 30 mg capsule of hydrazine sulfate daily for the first three days, then two such capsules daily for the next three days, and then two or three 30 mg capsules each day thereafter. For best results blood levels of hydrazine sulfate should be determined on these patients in order to establish a most effective non-toxic dose.

Hydrazine sulfate therapy can advantageously be combined with other modalities for cancer treatment like chemotherapy, immunotherapy, radiation and surgery.

Hydrazine sulfate is most effective when administered usually by itself one or two hours before meals in the form of a gelatin capsule. If desired, the sulfate can be dissolved or suspended in sterile, aqueous, isotonic saline solution and given orally and parenterally. Likewise, hydrazine sulfate can be formulated with solid carriers such as talc, corn starch or stearic acid and compressed into tablets for oral administration. Such tablets can be enteric coated with shellac or cellulose acetate phthalate in a manner well known to those skilled in the pharmaceutical art.

The efficacy of hydrazine sulfate in prolonging survival in early-stage human cancer patients has now been demonstrated for the first time in a placebo-controlled, double-blind experiment with a statistically significant number of subjects.

Early-stage human cancer patients are distinguished from late-stage human cancer patients on the basis of the nature of their symptoms. These symptoms have been quantitatively correlated by two recognized methods of categorization: the Eastern Cooperative Oncology Group (ECOG) Performance Status Score (also known as Zubrod's ) and the Karnofsky Rating Scale. The relationship between these two methods and the resulting division of human cancer patients into early-stage and late-stage, as recognized by ECOG and Karnofsky rating criteria, is set forth as follows:

| Stage of Cancer | ECOG Performance Status Score | Karnofsky Rating | Nature of Symptoms |
|---|---|---|---|
| Early | 0 | 100 | Asymptomatic without physical limitation |
| Early | 1 | 80–90 | Symptomatic, but fully ambulatory |
| Late | 2 | 60–70 | Symptomatic, but in bed less than 50% of day |
| Late | 3 | 40–50 | Symptomatic, in bed more than 50% of day, but not bedridden |
| Late | 4 | 20–30 | Bedridden |

In the placebo-controlled, double-blind experiemnt referred to above, to determine whether hydrazine sulfate treatment is associated with a survival benefit (R.T. Chlebowski et al., "Influence of Hydrazine Sulfate on Survival in Non-Small Cell Lung Cancer: A Randomized Placebo-Controlled Trial", presented at the Annual Meeting of the American Society for Clinical Oncology, May 17-19, 1987, Atlanta, Georgia), sixty-five patients with unresectable, non-small cell lung cancer and no prior chemotherapy were randomized to receive combination chemotherapy with either hydrazine sulfate or placebo addition for a period of up to four years. All received Platinol/Velban/Blenoxane (PVB) chemotherapy every 28 days, consisting of Platinol 100 mg/m$^2$; Velban 4 mg/m$^2$, days 1 and 2; and Blenoxane 10 units every 8 hours for three doses. After the initial three cycles, the Blenoxane was discontinued and the Platinol dose was reduced to 50 mg/m$^2$.

Pre-chemotherapy factors including age, sex, performance status (PS), prior weight loss and disease extent were comparable in the two groups, with pre-chemotherapy performance status (0– vs. 2) and prior weight loss (>10%) subsequently influencing overall survival ($p<0.05$). Toxicity was that expected from PVB with three patients not continuing hydrazine sulfate because of additional nausea. Survival by hydrazine sulfate or placebo were:

| Median Survival by Patient Group | | |
|---|---|---|
| Treatment Group | All Patients | PS 0-1 Patients |
| Hydrazine Sulfate | 292 days | 328 days* |
| Placebo | 173 days | 209 days |

Statistical analysis of the data was by the generalized Wilcoxon (Breslau) method. Comparison of the hydrazine sulfate and placebo groups showed statistical significance at the *$P<0.01$ level. All of the survival benefit of hydrazine sulfate was in the performance status 0-1 group. For the performance status (PS) 2 patients, whose condition was poor, survivals were short (median 132 days) and closely comparable whether on placebo or hydrazine sulfate. Thus, hydrazine sulfate addition, as an anti-cachexia agent directed primarily at correcting abnormal host mechanism, significantly increased patient survival in early-stage patients with non-small cell lung cancer.

Specifically, this increased survival time occurred in early-stage human cancer patients with Performance Status 0 or 1 (PS 0-1), whereas late-stage patients (PS 2) did not exhibit prolonged survival.

Several patients with tumors of the prostate, lung, breast, ovary, lymph, cervix, thyroid, pancreas and other tumor sites were treated with hydrazine sulfate according to the preferred regimen previously set forth.

I claim:

1. A method for prolonging patient survival in an early-stage human cancer patient which comprises internally administering to said human hydrazine sulfate in an effective dosage sufficient in amount and for a duration of from fourteen weeks to four years to prolong patient survival without treating a cancerous tumor per se.

2. The method of claim 1 wherein the hydrazine sulfate is administered orally in dosage form.

3. The method of claim 2 wherein the dosage form is a gelatin capsule or tablet.

4. The method of claim 1 wherein the hydrazine sulfate is administered parenterally.

5. The method of claim 1 wherein the dosage of hydrazine sulfate is 1 to 5 mg/kg of body weight daily.

6. The method of claim 1 wherein the hydrazine sulfate is administered in a daily regimen of one 60 milligram capsule for three days, then two 60 milligram capsules for the next three days, and three 60 milligram capsules each day thereafter for up to four years.

7. The method of claim 1 wherein the hydrazine sulfate is administered to patients weighing less than 100 pounds in a daily regimen of one 30 milligram capsule for three days, then two 30 milligram capsules for the next three days, then two or three 30 milligram capsules each day thereafter for up to four years.

* * * * *